United States Patent [19]

Le Tyrant

[11] Patent Number: 4,817,449
[45] Date of Patent: Apr. 4, 1989

[54] DEVICE FOR MOVING SAMPLES IN A CONTROLLED ATMOSPHERE ENCLOSURE

[76] Inventor: Claude Le Tyrant, 4, Place Pacquières, 78210 Nezel, France

[21] Appl. No.: 80,608

[22] Filed: Aug. 3, 1987

[30] Foreign Application Priority Data

Aug. 5, 1986 [FR] France .................................. 86 11327

[51] Int. Cl.⁴ ............................................. H01J 49/04
[52] U.S. Cl. .................................... 73/866.5; 250/442.1
[58] Field of Search ............. 73/864.81, 864.85, 866.5; 250/441.1, 442.1, 289; 356/244

[56] References Cited

U.S. PATENT DOCUMENTS

| | | | |
|---|---|---|---|
| 3,638,015 | 1/1972 | Browning et al. | 250/442.1 |
| 4,227,080 | 10/1980 | Okura et al. | 250/442.1 |
| 4,274,004 | 6/1981 | Kanai | 250/442.1 |
| 4,587,431 | 5/1986 | Uemura | 250/442.1 |

Primary Examiner—Stewart J. Levy
Assistant Examiner—Robert R. Raevis
Attorney, Agent, or Firm—Larson & Taylor

[57] ABSTRACT

The device comprises a sheath assembly defining an internal value opening into the enclosure. It further comprises a rack unit mounted in the sheath assembly for axial movement; a pinion mounted for rotation on said sheath assembly; meshing with said rack and rotatable from the outside of said sheath through a deformable sealed mechanical drive connection; a sample holder connected to said rack having a freely rotatable axial connection with said rack; and a drive rod slidably non-rotatably connected to said sample holder, fixed against axial movement with respect to the sheath assembly and rotatable from the outside of said sheath assembly through a deformable sealed mechanical drive connection, each of said connection being devoid of slidable joints.

5 Claims, 2 Drawing Sheets

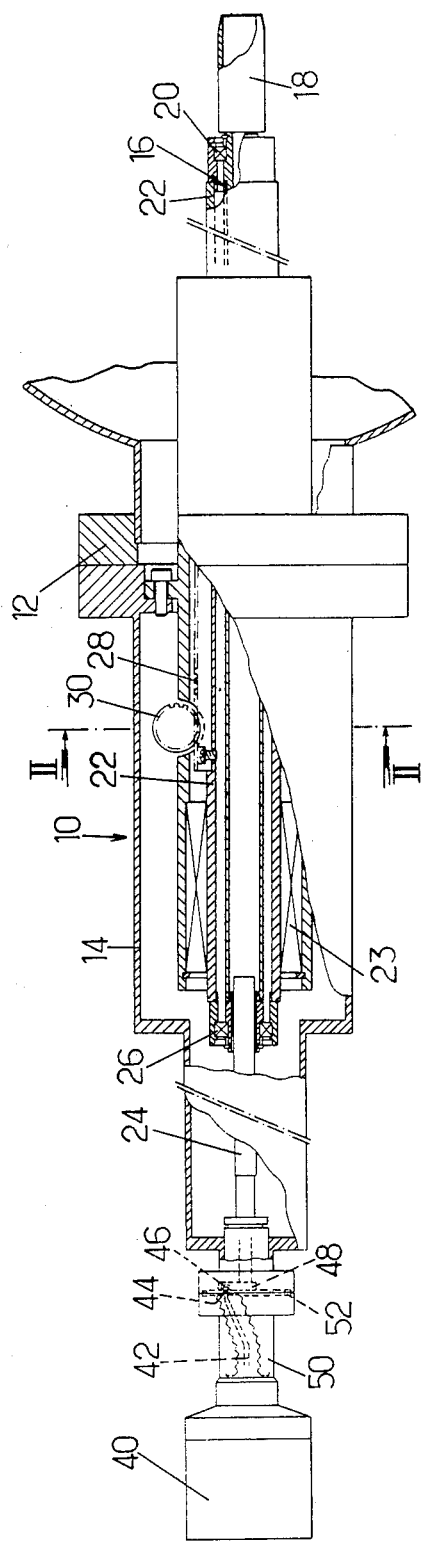
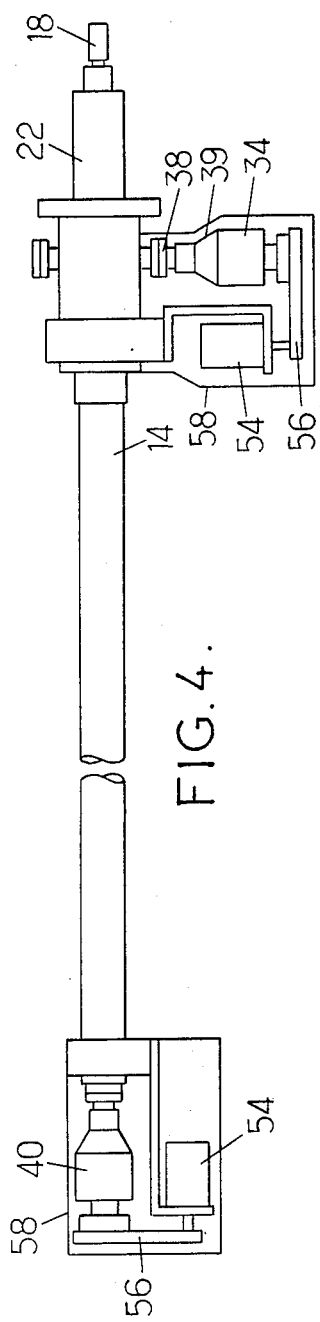

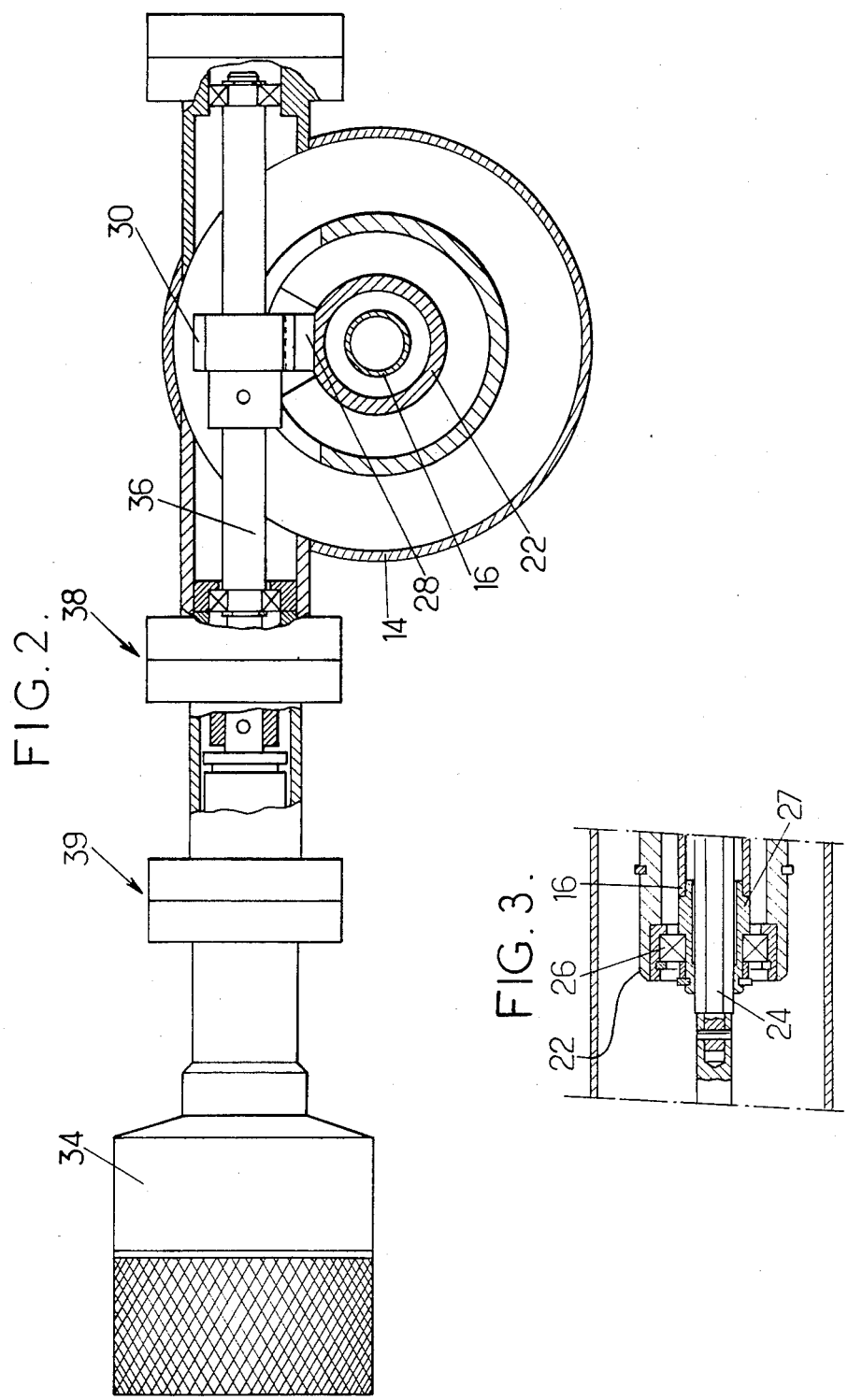

DEVICE FOR MOVING SAMPLES IN A CONTROLLED ATMOSPHERE ENCLOSURE

BACKGROUND OF THE INVENTION

The invention relates to devices for moving samples axially and in rotation in an evacuated enclosure. It is usable particularly for moving specimens in enclosures in which a high degree of vacuum exists, for example, in spectroscopy devices, where a vacuum of about $10^{-11}$ torr is necessary.

It is difficult to render seals between mutually movable elements and particularly sliding seals perfectly air-tight. When practically sealing of a transmission mechanism is necessary, recourse has consequently been had in the past to a magnetic drive. This type of drive has the drawback of not being positive: slippage can occur and render impossible the direct determination of the axial and angular position of the sample from the movements imposed on the actuating members. The use of magnets cannot be consiliated with the need of heating the parts to a high temperature for degasing.

One solution which appears a priori interesting, consists of using a sample-holder rod which sealingly projects through the bottom wall of sealing bellows coaxial with the direction of axial movement and is fixed thereto. In practice, this solution is no longer applicable when the amplitude of the movements is large, since it would require bellows which are much too long. Movements of more than one meter are often necessary for spectrometry.

SUMMARY OF THE INVENTION

It is an object of the invention to provide an improved driving device which does not impose any limit on the amplitude of the movements whilst guaranteeing complete gas tightness.

Accordingly, the invention provides a device which comprises, in a sheath assembly arranged for connection with the enclosure:

a rack mounted in the enclosure for axially slidable movement, meshing with a pinion rotatable from the outside of the enclosure through a deformable sealed mechanical connection.

a sample holder driven in the axial direction by said rack, but free in rotation with respect to it, a drive rod for rotating the sample holder, fixed against axial movement with respect to the enclosure, slidably non rotatably connected to the sample holder and rotatable from the outside through a deformable sealed mechanical connection.

The passage through wall means are through sealed joints without sliding movement and consequently sealing can be complete. Considering that the connections used are positive, there is no risk of slippage. The slidable keying of the sample holder enables rotary movements to be transmitted from a drive rod fixed against axial movement. The connection can be of small size. The latter may typically use so-called "cat's tail" drive mechanisms, employing deformable bellows.

All parts will typically be of molybdenum containing stainless steel which does not release gas when subjected to a vacuum.

The invention will be better understood from the following description of a particular embodiment, given by way of example.

SHORT DESCRIPTION OF THE DRAWINGS

The description refers to the accompanying drawings, in which:

FIG. 1 is an overall view of the sample-moving device in elevation and in partial longitudinal section;

FIG. 2 shows diagrammatically the rotary drive connection from the outside, in section along line II-II of FIG. 1.

FIG. 3 is a view on an enlarged scale illustrating the slidable non-rotatable connection between the sample holder and the drive rod of FIG. 1.

FIG. 4 is an elevational view of a modified embodiment.

DETAILED DESCRIPTION

The sample-moving device shown in FIGS. 1 and 2 can be mounted on the wall 12 of the intake chamber of an apparatus operating under a hard vacuum, such as a spectrometer (not shown). It permits the sample to be moved between the spectrometer and the chamber, separated from the spectrometer by a door to be opened for transfer of the sample between the chamber and the spectrometer. Another air tight door provides an access to the chamber from the outside.

The device as shown comprises a sealing sheath assembly 14 consisting of a plurality of assembled parts, fixed around an aperture for passage through the wall 12 and a movable mechanism inside the sheath.

This mechanism comprises a stick 16 terminated by a sample receiving holder 18. The stick 16 is carried through a bearing 20, by a tube 22 axially movable within and along the sheath assembly 14. A ball bushing 23 is located between tube 22 and sheath assembly 14. The tube 22 belongs to a unit axially movable with respect to the axially-fixed rod 24 of a rotary drive mechanism having a non-rotatable axially slidable connection with the stick 16. The rod 24 is guided along the axially movable unit by ball bearing 26. As shown in FIG. 3, the rod 24 has a polygonal (typically hexagonal) cross-section and is slidably received in an end insert 27 of the stick 16, having an internal shape corresponding to that of the rod.

The mechanism for axially driving tube 22 and stick 16 comprises a rack 28 fixed to the tube 22 and meshing with a pinion 30 rotatable by a knurled knob 34 located outside of the enclosure via a sealed mechanical connection. As shown, the pinion 30 is fixed to a rod 36 connected to the rotary knob 34 by a union 38 and a sealed coupling 39.

The rod 24 is rotated by an external knurled knob 40, through a sealed mechanical coupling which may be identical to the sealed mechanical coupling for axial control. In order that they may be sufficiently air-tight when under a vacuum, they do not include sliding joints. In practice, each coupling may be a deformable sealed coupling of the type currently known as "cat's tail" will typically be used. Such a coupling is shown diagrammatically in FIG. 1 and comprises a crank-shaped rod 42 secured to the corresponding knob 40 and having a branch directed along the axis of the rod. The free end of the bent rod engages onto an excentrically located cup 46 formed in the bottom wall 44 of a deformable metal bellows. The cup protrudes into a hole formed in a crank 48 secured to the terminal portion of the rod 24. The open end of the bellows is fixed directly, for example by welding, to a housing 50. The connection between the housing 50 and the sheath assembly 14 can be rendered air tight without difficulty by means of a seal 52 since the seal is located between mutually fixed parts. The deformable mechanical connection may be the component named TRMP available from MECA2000.

In a modified embodiment, the knurled knob 40 is replaced with a tube which surrounds the mechanism and extends up to the and flange for connection with wall 12. A knurled ring is fixed to that surrounding tube for rotating the stick. Such an arrangement is more convenient for the user when the sheath assembly has a considerable length.

Referring to FIG. 4, the movements are controlled by electric motors in a modified embodiment. Such motors are DC motors or preferably step-by-step motors 54 which drive the knobs 34 and 40 through a toothed belt 56. Each motor and associated belt are located in a protection housing 58. Such an arrangement makes it possible to control the movements remotely. The movements may be monitored with a TV camera carried by the chamber (not shown).

I claim:

1. A device for moving samples in an evacuated enclosure, comprising: a sheath assembly defining an internal volume and arranged for connection with the enclosure; a rack unit mounted in the sheath assembly for axial movement; a pinion mounted for rotation on said sheath assembly, meshing with said rack unit and rotatable from the outside of said sheath assembly through a deformable sealed mechanical drive connection, a sample holder connected to said rack unit having a freely rotatable axial connection with said rack unit; and a drive rod having a slidable non-rotatable connection with said sample holder, fixed against axial movement with respect to the sheath assembly and rotatable from the outside of said sheath assembly through a deformable sealed mechanical drive connection, each of said connections being positive and devoid of slidable joints.

2. A device according to claim 1, wherein each of said sealed mechanical drive connections comprises a cat's tail mechanism projecting through the bottom wall of a sealing metal bellows.

3. A device according to claim 1, wherein said rack unit includes a tube and the rack unit securely connected to the tube and said sample holder includes a stick located within the tube and coaxial thereto.

4. A device according to claim 3, wherein said drive rod has a polygonal cross section and is axially slidable along guide means of corresponding shape fixed to said stick.

5. A device for moving samples in an evacuated enclosure; comprising:
 a sheath assembly defining an internal volume and arranged for connection with the enclosure;
 a rack mounted in the sheath assembly for axial movement;
 a pinion mounted for rotation on said sheath assembly, meshing with said rack and rotatable from the outside of said sheath assembly through a deformable sealed mechanical positive drive connection;
 a sample holder connected to said rack having a freely rotatable axial connection with said rack;
 and a drive rod having a slidable non-rotatable connection with said sample holder, fixed against axial movement with respect to the sheath assembly and rotatable from the outside of said sheath assembly through a deformable sealed mechanical positive drive connection including a cat's tail mechanism projecting through the bottom wall of a sealing metal bellows.

* * * * *